United States Patent [19]

Maude et al.

[11] 4,233,264
[45] Nov. 11, 1980

[54] APPARATUS FOR PRODUCING A GASEOUS HYDROCARBON/AIR MIXTURE AND FOR THE CATALYTIC OXIDATION OF THIS MIXTURE

[75] Inventors: John H. Maude, Cologne; Lothar Sterck, Hürth; Alfred Vilshöfer, Elsdorf, all of Fed. Rep. of Germany

[73] Assignee: Davy International AG, Frankfurt, Fed. Rep. of Germany

[21] Appl. No.: 950,794

[22] Filed: Oct. 12, 1978

[30] Foreign Application Priority Data

Oct. 12, 1977 [DE] Fed. Rep. of Germany ....... 2745765

[51] Int. Cl.³ .......................... B01J 3/04; B01J 10/00; B01J 8/06; G05B 9/00
[52] U.S. Cl. .................................... 422/117; 422/190; 422/197; 422/202; 422/208; 422/211; 422/217; 422/220; 260/346.3; 260/346.4; 260/346.7
[58] Field of Search .............. 422/157, 117, 197, 208, 422/220, 242, 189, 190, 202, 211, 217; 260/346.3, 346.4, 346.7

[56] References Cited

U.S. PATENT DOCUMENTS

| | | | |
|---|---|---|---|
| 1,909,358 | 5/1933 | Jaeger | 422/197 |
| 1,917,718 | 7/1933 | Jewett | 422/197 |
| 2,698,330 | 12/1954 | Fugate et al. | 260/346.4 |
| 2,986,454 | 5/1961 | Jewett | 422/197 |
| 3,296,281 | 1/1967 | Hughes | 260/346.7 |
| 3,353,923 | 11/1967 | Peters | 260/346.4 |

Primary Examiner—Bradley R. Garris
Attorney, Agent, or Firm—Bernard & Brown

[57] ABSTRACT

Apparatus for the production and catalytic oxidation of gaseous hydrocarbon/air mixtures to form dicarboxylic acid anhydride. Hydrocarbon/air mixtures are formed in an evaporator and introduced into a shell-and-tube catalytic reactor fitted with a concave reactor hood to more effectively and safely distribute the gaseous mixture to and through the catalyst-filled tubes of the reactor.

11 Claims, 1 Drawing Figure

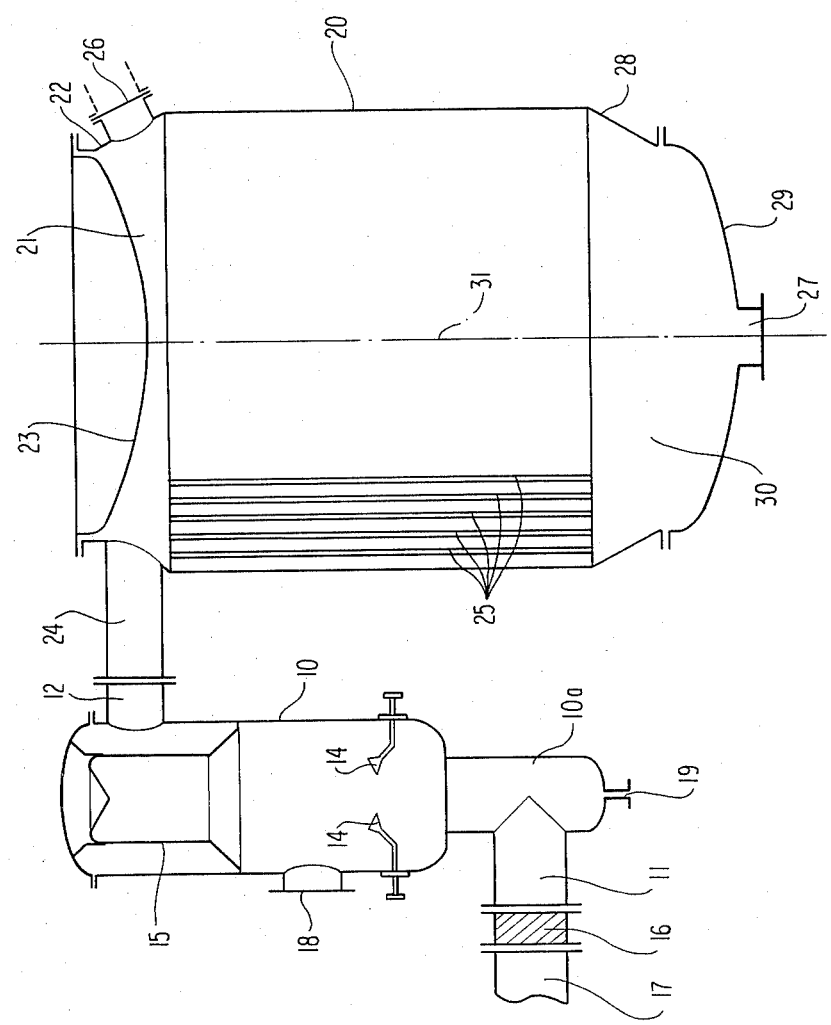

APPARATUS FOR PRODUCING A GASEOUS HYDROCARBON/AIR MIXTURE AND FOR THE CATALYTIC OXIDATION OF THIS MIXTURE

The invention relates to an apparatus for the production of a gaseous hydrocarbon/air mixture and for catalytic oxidation of this mixture with formation, for example, of dicarboxylic acid anhydride. The apparatus comprises an evaporator with an air inlet pipe on its inflow side, an outlet pipe for the mixture on its outflow side and at least one nozzle arranged between the pipes for the injection of hydrocarbon. Such an evaporator is in communication with a shell-and-tube reactor having a plurality of parallel tubes which are filled with catalyst and are cooled externally, for example, by a salt melt. Such a reactor is fitted with an at least partially concave hood on the inflow side of said reactor, said hood being connected to the mixture outlet pipe of the evaporator.

Processes and apparatus are known with which heated, liquid o-xylene is injected into an air stream which is heated to a temperature in the range from 120° to 190° C., the o-xylene is evaporated in the air stream, the mixture is homogenized and the stream of the o-xylene/air mixture is divided into a plurality of vertical, parallel component streams, which are brought at a temperature in the range from 380° to 440° C. into contact with a catalyst. The apparatus for carrying this process into effect generally consists of an evaporator with an air inlet pipe on its inflow side, a mixture outlet pipe on the outflow side and at least one nozzle arranged between the pipes for the injection of o-xylene into the evaporator. Such apparatus also consists of a shell-and-tube reactor with a plurality of parallel tubes which are filled with catalyst and which are cooled externally by a salt melt. The reactor hood on the inflow side is connected to the mixture outlet pipe of the evaporator. Very similar processes and apparatus are known for the production and oxidation of mixtures of benzene or $C_4$ hydrocarbons (butane, butylene) and air, and also of naphthalene and air.

The known processes and apparatus have been developed for mixtures having hydrocarbon concentrations below the lower ignition limit, i.e., as regards o-xylene/air mixtures, for example, below 44 gm. of o-xylene/$m^3$ of air (at n.t.p., i.e., normal temperature and pressure, 0° C. and 1 atm.) more especially at about 40 gm. of o-xylene/$m^3$ of air (at n.t.p.). It has now been recognized that by increasing the hydrocarbon concentration in the gas mixture to be oxidized to a level above the lower ignition limit, a considerable increase in production is achieved with an equipment of the same size. Also the heat being liberated with the catalytic oxidation of such higher strength mixtures may be better utilized. When the air is charged with concentrations of hydrocarbon above the ignition limit, however, the danger of explosion exists in those parts of the equipment in which there is an ignitable hydrocarbon/air mixture, i.e., in the evaporator, the reactor hood at the inflow side of the reactor, in the pipe connection between evaporator and reactor and also in the upstream ends of the catalyst tubes. For this reason, it has not hitherto been possible technically to carry out the catalytic oxidation of hydrocarbons with air to form dicarboxylic acid anhydrides by using a hydrocarbon/air mixture having hydrocarbon concentrations above the lower ignition limit.

The object of the invention is to provide an apparatus for the production of a hydrocarbon/air mixture and for the subsequent catalytic oxidation of this mixture to form, for example, dicarboxylic acid anhydride, with which mixture the danger of explosion in the critical section of the plant is substantially reduced, so that when safety measures which are usual for ignitable gas mixtures are maintained, it is possible to have a trouble-free operation on a large industrial scale.

According to the invention, this object is achieved by modifying the apparatus as described above by outfitting the reactor hood on the inflow side with one surface which is at least partially curved inwardly, i.e., concave. As a result of the shape of the reactor hood being concave, when looking from outside onto the hood, a uniform distribution of the gas mixture to the catalyst tubes is achieved with a minimal hood volume. By the formation of the layer of gas in the hood, which layer becomes thinner towards the reactor axis, the volume of the ignitable mixture is kept relatively small, so that the effect is restricted in the event of an explosion. The inward curvature may extend over the entire reactor cross section or only over a part thereof. The reactor hood on the outflow side of the reactor is curved outwardly in the conventional manner, since generally there is no longer any danger of explosion after oxidation of the gas mixture has taken place.

Using the apparatus according to the invention, o-xylene or naphthalene can be processed into phthalic acid anhydride and benzene or $C_4$-hydrocarbons (butane, butylene) can be processed into maleic acid anhydride. For this purpose, the operation is carried out with charges of 40 to 250, advantageously 40 to 95, and more especially 50 to 70 gm. of o-xylene per $m^3$ of air (at n.t.p.), 40 to 320, advantageously 40 to 100, more especially 50 to 80 gm. of naphthalene/$m^3$ of air (at n.t.p.), 35 to 270, advantageously 35 to 100, more especially 45 to 70 gm. of benzene/$m^3$ of air (at n.t.p.), 35 to 210, advantageously 35 to 90, more especially 40 to 60 gm. of butane/$m^3$ of air (at n.t.p.) and 30 to 230, advantageously 30 to 90, more especially 40 to 60 gm. of butylene/$m^3$ of air (at n.t.p.).

In accordance with the preferred embodiment of the invention, the reactor hood on the inflow side is concave, i.e., curved inwardly, in the form of an inverted dished head. The inverted dished head permits a substantial reduction of the hood volume, so that gas-displacement bodies installed in the hood can be dispensed with. In accordance with one embodiment, the reactor hood is in the form of a frustoconical member having an inverted dished head flanged on its upper peripheral edge. This constructional form is suitable for large reactors, because the dished head can be fitted on with a flange diameter which is reduced compared with the reactor diameter and an easy access to the upper tube plate, for example, for the purpose of introducing catalyst into the tubes, is possible. As regards reactors which are of medium and relatively small size, the inverted dished head is expediently welded to the upper peripheral edge of the frustoconical hood member. The flange connection of the hood is then arranged on the lower circumferential edge of the frustoconical member and on the tube plate of the reactor.

The reactor hood on the inflow side is preferably provided with a radial inlet pipe for the mixture, which pipe is directly connected to the outlet pipe of the evaporator. The evaporator has a direct flanged connection to the reactor. With large reactors, the mixture outlet pipe of the evaporator may be directly welded to the gas inlet pipe on the truncated cone of the upper reactor hood, since the truncated cone of the hood with large reactors is welded fast to the tube plate.

It is advantageous for the air inlet pipe to be arranged beneath the nozzle and for the mixture outlet pipe to be arranged above the nozzle on the evaporator housing. The liquid hydrocarbon is thus injected into an upwardly directed air stream and is completely evaporated along a short flow path. It is also possible in this way for the evaporator to be installed at the same height as the reactor and for a relatively long pipe conduit between the two apparatus to be avoided.

According to the preferred embodiment of the invention, a screening layer or bed is arranged in the evaporator between the nozzle and the outlet pipe for the mixture. The said screening bed or layer causes a homogenization of the hydrocarbon/air mixture. In addition, in the event of an explosion, it prevents the penetration of the pressure wave and of the flame zone. Droplets of hydrocarbon which are not vaporized are separated by the screening bed from the flow of the mixture. The droplets may possibly drip back into the upwardly flowing stream of the mixture and thus be completely vaporized.

The screening layer arranged downstream of the nozzles is preferably constructed as a metal basket with a smooth surface, fixed on the cover of the evaporator. Such a construction guarantees, firstly, an adequate homogenization of the gas mixture; secondly, the probability of an ignition of the mixture on the smooth and preferably polished surface is small. The flange-connected evaporator cover forms an assembly unit with the metal basket which is fixed thereon, as a result of which the maintenance of the screening basket is facilitated.

The evaporator housing is preferably a substantially cylindrical container having an axis which is parallel to the tube axis, and at the lowest point of which is arranged an outlet pipe for hydrocarbon which is not vaporized. Since the accummulation of non-vaporized hydrocarbon indicates an inefficient vaporization, which may also result in an increased danger of explosion, the evaporation is in this case preferably interrupted. The lower section of the evaporator housing may have a smaller diameter than the upper section, so that droplets of hydrocarbon falling into the lower section are again forced upwardly, because of the higher air velocity in this lower section, and can be further vaporized.

It is also possible for a screening layer or bed to be provided in the evaporator housing on the inflow side of the nozzles or in the air inlet pipe. In the event of an explosion in the evaporator, this screening bed reduces the pressure wave passing over into the air inlet pipe.

The invention is hereinafter more fully described by reference to the drawing, in which a cross section of an embodiment of the apparatus according to the invention is shown.

The preheated air flows from a pipe 17 through the screening layer or bed 16 and the air inlet pipe 11 into the lower section 10a of the evaporator 10. In the said lower section 10a, the air is deflected vertically upwards and preheated o-xylene is added to it in the upper section of the evaporator through the nozzles 14. The major part of the sprayed-in o-xylene evaporates in the upwardly flowing hot air; the mixture leaves the evaporator 10, after passing through the screening bed 15, through the outlet pipe 12 for the mixture. The screening bed 15, which is in the form of a basket, consists for example of polished stainless steel and causes a substantial homogenization of the mixture and a separation from the gas stream of o-xylene which has possibly not been evaporated. The o-xylene which has not evaporated accumulates in the lower section 10a of the evaporator and can be drawn off by way of a pipe 19. The evaporator 10 is equipped with a pressure-relief opening 18.

The homogeneous o-xylene/air mixture flows directly through the pipe 24 into the upper hood 21 of the reactor 20. The hood 21 has a frustoconical wall 22, on to the upper circumferential edge of which is flanged an inwardly curved dished head 23. The gas mixture is distributed uniformly to the reactor tubes 25 in the interior of the hood 21. The reaction gas accumulates in the lower reactor hood 30, which consists of a frustoconical part 28 and an outwardly curved dished head 29, and is carried away via pipe 27.

Arranged in the frustoconical region 22 of the upper reactor hood are several pressure-relief openings 26, of which only one is shown. In this way, in the event of an explosion in the upper reactor hood 21, the maximum explosion pressure in the latter is substantially reduced and the reactor 20 is not stressed beyond its compressive strength.

The invention is not limited to the constructional form which has been illustrated; instead of the dished head, it is also possible to use other inwardly curved plates, as for example basket-type heads, pressure boiler heads, tank heads and similar heads, which make it possible for the explosive gas mixture to be distributed to the reactor tubes in a layer which becomes progressively thinner towards the common axis 31 of all the reactor tubes 25 which are filled with catalyst.

The invention extends also to embodiments in which the hydrocarbon is initially vaporized and then the vaporous hydrocarbon is mixed with air. This separation of evaporator or vaporizer and mixing assembly is generally used when employing naphthalene or butane/butene as the hydrocarbon.

What is claimed is:

1. Apparatus for forming a gaseous hydrocarbon/air mixture and for subsequently catalytically oxidizing said mixture, said apparatus comprising an evaporator having an air inlet pipe on the inflow side of said evaporator, an outlet pipe for said mixture on the outflow side of said evaporator and at least one injection nozzle positioned between said inlet and outlet pipes suitable for injecting hydrocarbon into said evaporator, and a shell-and-tube reactor comprising a plurality of parallel, externally cooled, catalyst-filled tubes, a hood on the upstream side of the tubes and a hood on the downstream side of the tubes, said hood on the downstream side being substantially convex-shaped as viewed from the exterior of said reactor and said hood on the upstream side being substantially concave-shaped as viewed from the exterior of said reactor such that the volume of the upstream hood is substantially reduced compared with the volume of an outwardly curved hood, said upstream hood being in communication with the outlet pipe of said evaporator.

2. Apparatus according to claim 1 wherein a screening layer or bed is positioned in the evaporator between the hydrocarbon injection nozzle and the mixture outlet pipe.

3. Apparatus according to claim 1 wherein the upstream hood includes an inverted dished head.

4. Apparatus according to claim 3 wherein the upstream hood is constructed in the form of a frustoconical member with the inverted dished head flanged on the upper peripheral edge of said member.

5. Apparatus according to claim 4 wherein the upstream hood is provided with a radial inlet pipe which is directly connected to the outlet pipe of said evaporator.

6. Apparatus according to claim 5 wherein the evaporator is constructed such that the air inlet pipe of said evaporator is positioned below the hydrocarbon injection nozzle of said evaporator and the mixture outlet pipe is positioned above said hydrocarbon, injection nozzle.

7. Apparatus according to claim 6 wherein a screening layer or bed is positioned in the evaporator between the hydrocarbon injection nozzle and the mixture outlet pipe.

8. Apparatus according to claim 7 wherein the screening layer or bed is formed as a basket with a smooth surface, the basket being mounted on a cover for the evaporator.

9. Apparatus according to claim 8 wherein the evaporator is a substantially cylindrical container having its axis parallel to the axis of the shell-and-tube reactor and wherein an additional outlet pipe for nonevaporated hydrocarbon is positioned in communication with said evaporator at the lowest point on said evaporator.

10. Apparatus according to claim 9 wherein a screening layer or bed is positioned in the air inlet pipe of said evaporator.

11. A shell-and-tube reactor for catalytically oxidizing a stream of a gaseous hydrocarbon/air mixture, said reactor comprising a plurality of parallel, externally cooled, catalyst-filled tubes, a hood on the upstream side of said tubes and a hood on the downstream side of said tubes, said hood on the downstream side being substantially convex-shaped as viewed from the exterior of said reactor and said hood on the upstream side being substantially concave-shaped as viewed from the exterior of said reactor such that the upstream hood volume is substantially reduced compared with an outwardly curved hood.

* * * * *